United States Patent
Højlund Nielsen et al.

(10) Patent No.: US 11,319,284 B2
(45) Date of Patent: May 3, 2022

(54) PROCESS FOR THE SYNTHESIS OF NITRILES

(71) Applicant: HALDOR TOPSØE A/S, Kgs. Lyngby (DK)

(72) Inventors: Poul Erik Højlund Nielsen, Fredensborg (DK); Burcin Temel McKenna, Hellerup (DK); John Bøgild Hansen, Humlebæk (DK); Rasmus Munksgård Nielsen, Måløv (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 336 days.

(21) Appl. No.: 16/096,493

(22) PCT Filed: Apr. 24, 2017

(86) PCT No.: PCT/EP2017/059598
§ 371 (c)(1),
(2) Date: Oct. 25, 2018

(87) PCT Pub. No.: WO2017/186615
PCT Pub. Date: Nov. 2, 2017

(65) Prior Publication Data
US 2019/0144376 A1    May 16, 2019

(30) Foreign Application Priority Data
Apr. 26, 2016  (DK) .......................... PA 2016 00246

(51) Int. Cl.
| | | |
|---|---|---|
| *C07C 253/18* | (2006.01) | |
| *B01J 8/02* | (2006.01) | |
| *C07C 253/00* | (2006.01) | |
| *H05B 6/10* | (2006.01) | |
| *B01J 23/14* | (2006.01) | |
| *B01J 23/75* | (2006.01) | |
| *B01J 35/00* | (2006.01) | |
| *C07C 255/03* | (2006.01) | |

(52) U.S. Cl.
CPC ........... *C07C 253/18* (2013.01); *B01J 8/0285* (2013.01); *B01J 23/14* (2013.01); *B01J 23/75* (2013.01); *B01J 35/0033* (2013.01); *C07C 253/00* (2013.01); *H05B 6/108* (2013.01); *B01J 2208/00433* (2013.01); *B01J 2208/00469* (2013.01); *C07C 255/03* (2013.01)

(58) Field of Classification Search
CPC ................................................... C01C 3/0229
See application file for complete search history.

(56) References Cited

U.S. PATENT DOCUMENTS

| | | | |
|---|---|---|---|
| 3,948,645 A | 4/1976 | Elvander et al. | |
| 5,110,996 A | 5/1992 | Edwards | |
| 5,958,273 A | 9/1999 | Koch et al. | |
| 6,315,972 B1 | 11/2001 | Mehdizadeh et al. | |
| 8,906,334 B2 * | 12/2014 | Slaten ................... | B01J 8/0285 423/372 |
| 2012/0141345 A1 | 6/2012 | Slaten | |
| 2016/0023201 A1 | 1/2016 | Chaudret et al. | |

FOREIGN PATENT DOCUMENTS

| | | |
|---|---|---|
| CN | 101687658 A | 3/2010 |
| DK | 201500118 A1 | 3/2015 |
| EP | 1480740 B1 | 4/2009 |
| FR | 3003774 A1 | 10/2014 |
| GB | 2210286 A | 6/1989 |
| JP | 2002510248 A | 4/2002 |
| JP | 2005519832 A | 7/2005 |
| WO | 9521126 A1 | 8/1995 |
| WO | 9615983 A1 | 5/1996 |
| WO | 9901212 A1 | 1/1999 |
| WO | 03078054 A1 | 9/2003 |
| WO | 2014162099 A1 | 10/2014 |

OTHER PUBLICATIONS

Houlding et al., "Application of alternative energy forms in catalytic reactor engineering", Green Processing and Synthesis, Jan. 2012, pp. 19-31, vol. 1, No. 1.
International Search Report (PCT/ISA/210) dated Jul. 17, 2017, by the European Patent Office as the International Searching Authority for International Application No. PCT/EP2017/059598.
Search Report dated Nov. 25, 2016, by the Danish Patent Office for Application No. PA 2016 00246.
Written Opinion (PCT/ISA/237) dated Jul. 17, 2017, by the European Patent Office as the International Searching Authority for International Application No. PCT/EP2017/059598.
Office Action (Notice of Reasons for Refusal) dated Jan. 20, 2021, by the Japanese Patent Office in corresponding Japanese Patent Application No. 2018-555931, and an English Translation of the Office Action. (10 pages).
Office Action (The First Office Action) dated Jan. 8, 2021 by the China National Intellectual Property Administration in corresponding Chinese Patent Application No. 2017800252818.8, and an English Translation of the Office Action. (11 pages).

* cited by examiner

*Primary Examiner* — Joseph R Kosack
(74) *Attorney, Agent, or Firm* — Buchanan Ingersoll & Rooney P.C.

(57) ABSTRACT

In a process for the synthesis of a nitrile by endothermic catalyzed reaction of ammonia with a hydrocarbon using heating obtained by passing an alternating current through a metallic coil, the endothermic reaction between ammonia and the hydrocarbon takes place in a reactor with direct inductive heating in the reaction zone. The heating is extremely fast, which makes the reaction practically instantaneous.

13 Claims, 1 Drawing Sheet

PROCESS FOR THE SYNTHESIS OF NITRILES

TECHNICAL FIELD

The present invention relates to a process for the synthesis of nitriles. More specifically, the invention relates to a process for the synthesis of nitriles using inductive heating.

BACKGROUND AND SUMMARY

The non-oxidative synthesis of nitriles, such as hydrogen cyanide, acetonitrile, acrylonitrile and other nitriles, like propionitrile and methacrylonitrile, is a high temperature process which takes place between 700 and 1000° C. The high heat needed for the synthesis of these nitriles can be provided electrically or inductively, with the advantage that the heat is provided faster to the reactant feed compared to using traditional ways of heating.

A method of inductively igniting a gas phase chemical reaction in the presence of a solid catalyst is disclosed in WO 99/01212. Specifically, this document describes a continuous-flow gas phase reaction wherein ammonia reacts with a hydrocarbon in the presence of oxygen and a platinum-group metal catalyst, which can consist of a plurality of layers of platinum metal wire, fabric or gauze, to produce hydrogen cyanide (HCN). An induction coil within the reactor is used to inductively heat the metallic catalyst and ignite the exothermic reaction.

WO 03/078054 describes a process for the production of HCN by reacting ammonia with methane by direct inductive heating in a reactor. The catalyst/susceptor is a platinum group metal or a Pt/Rh or Pt/Ir alloy with various possible structures, and the reaction can be directly heated by an inductive coil surrounding the catalyst/susceptor.

In U.S. Pat. No. 6,315,972, a process for the production of HCN by direct inductive heating is de-scribed. The catalyst comprises multiple susceptor entities, e.g. pellets, rings or rods containing the catalyst, e.g. a platinum group metal or a Pt/Rh or Pt/Ir alloy, as a foam.

The concept of using inductive heating to heat a catalyst during a gas phase chemical reaction at elevated temperature is generally known in the art. Thus, in U.S. Pat. No. 5,110,996, a process is disclosed, in which vinylidene fluoride is produced by reacting dichlorofluoromethane with methane in an inductively heated reaction tube containing a non-metallic packing material and optionally a metallic catalyst.

Similarly, WO 95/21126 discloses the preparation of HCN by reacting ammonia and a hydrocarbon gas in an inductively heated quartz reactor tube. A platinum group metal catalyst within the reactor tube is heated by the presence of an inductive coil helically wound around the exterior of the quartz tube, said coil being energized by an induction power source which also supplies pulsed power. For the particular endothermic reaction being employed, a frequency range of 0.5-30 MHz is suggested to maintain the reaction temperature between 600 and 1200° C. The induction coil wrapped around the exterior of the reactor tube is itself a metal tube through which cooling water is being circulated.

Generally, inductive heating is the process of heating an electrically conducting object (which usually is a metal) by magnetic induction, through heat generated in the object by eddy currents (also called Foucault currents, which are loops of electrical current induced within conductors by a changing magnetic field in the conductor, due to Faraday's law of induction) and/or by hysteresis loss. Eddy currents flow in closed loops within conductors, in planes perpendicular to the magnetic field.

An induction heater consists of an electromagnet and an electronic oscillator which passes a high-frequency alternating current (AC) through the electromagnet. The rapidly alternating magnetic field penetrates the object, whereby electric currents inside the conductor, called eddy currents, are generated. The eddy currents flowing through the resistance of the material will heat it by Joule heating. Eddy current heating is also denoted ohmic heating. In ferromagnetic (and ferrimagnetic and antiferromagnetic) materials like iron, heat may alternatively or additionally be generated by magnetic hysteresis losses. This is denoted ferromagnetic heating. The frequency of the current used depends on the object size, material type, coupling (between the induction coil and the object to be heated) and the penetration depth. An induction coil comprising a conductor bent into the form of a plurality of loops or windings is an example of an electromagnet.

Heating of ferromagnetic materials is relatively faster and cheaper than heating of non-ferromagnetic materials. A ferromagnetic material has an inherent or intrinsic maximum temperature of heating, viz. the Curie temperature. Therefore, the use of a catalyst material which is ferromagnetic ensures that an endothermic chemical reaction is not heated beyond a specific temperature, viz. the Curie temperature. Thus, it is ensured that the chemical reaction will not run out of control.

Inductive heating is generally carried out using an alternating current, often of high frequency, which is passed through a coil. The subject to be heated is placed inside the coil. This procedure is, however, not very energy efficient, because the magnetic field generated by the coil will continue also outside the coil. While this drawback may be avoided by shaping the coil as a torus, there will still be a loss due to the resistance in the coil, i.e. the ohmic heat, which normally will be lost for the process.

It has now turned out that it is possible to establish a much more energy efficient approach. In said approach, the coil will be mounted within the reactor, and the catalyst will be placed inside the coil. This way, the ohmic heat will not be lost for the process, and provided that the pressure shell is based on iron with a low hysteresis, or alternatively that the pressure shell is coated on the inside with such iron type, the magnetic field generated by the coil will not be able to penetrate out of the reactor. At very high temperatures, the reactor may be walled up and possibly cooled to protect it by keeping the temperature below the Curie temperature, which is the temperature at which certain materials lose their permanent magnetic properties, to be replaced by induced magnetism. Typically, the coil can be made of KANTHAL-type (Fe—Cr—Al alloy) wire, which resists reducing gases. The coil can also be made of copper wire, constantan wire and wire made of an iron-chromium-aluminium (FeCrAl) alloy, an alloy of copper, manganese and nickel and combinations thereof. Preferably the coil is made of KANTHAL-type (Fe—Cr—Al alloy) wire.

The coil may be placed so that it has a direct electrical contact to the catalyst. In this case, an additional ohmic heating of the catalyst will take place. In addition, there will be no need for electrical isolation of the coil.

DETAILED DESCRIPTION

Thus, the present invention relates to a process for the synthesis of a nitrile by catalyzed reaction of ammonia with a hydrocarbon using heating obtained by passing an alternating current through a metallic coil, wherein the endothermic reaction between ammonia and the hydrocarbon takes place with direct inductive heating in the reaction zone.

Figure 1:
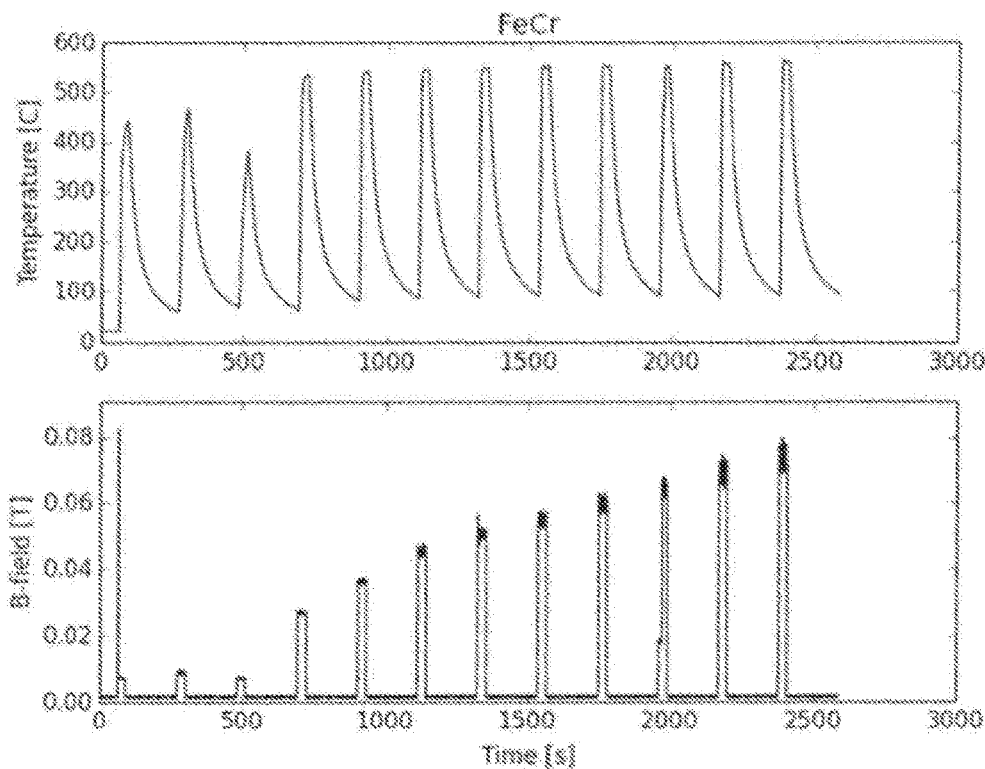
FIG. 1 shows how the temperature of an Fe—Cr alloy subjected to varying magnetic fields develops as a function of time.
Figure 2:
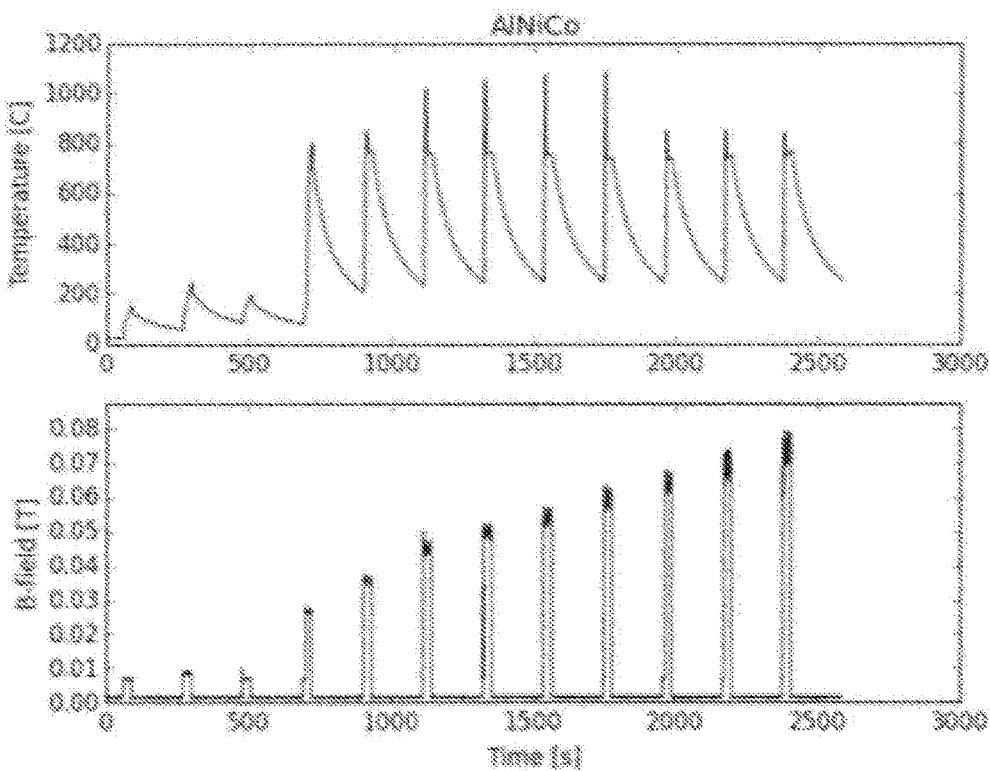
FIG. 2 shows how the temperature of an Al—Ni—Co alloy subjected to varying magnetic fields develops as a function of time.

Induction heating enables heating with a heat output of more than 70 W/g, which gives heating rates of more than 150° C./s. Thus, induction heating offers a way of very fast and effective heating. This is illustrated in FIG. 1 and FIG. 2 showing how the temperature of Fe—Cr and Al—Ni—Co alloys subjected to varying magnetic fields develops as a function of time.

Among the possible combinations of a ferromagnetic structure and a suitable coating, the best cases were found to be those in which the structure is composed of metals of Fe—Cr or Al—Ni—Co alloys.

The Fe—Cr alloy has a Curie temperature, which is the temperature at which certain materials lose their permanent magnetic properties, of around 560° C. The coating is oxide-based, and it can be an oxide made of a combination of Al, Zr, Ce etc.

The coated metal structure has a porous oxide surface which can be impregnated with practically any catalytic phase. It can therefore be matched to any conventional catalysts for nitrile synthesis, such as catalysts based on Co and Sn.

It may be difficult to obtain sufficient activity in this manner. Thus, an alternative possibility is to dilute the conventional catalyst with a magnetic material.

Since the heating is supplied from inside the reactor, which makes the catalyst the hottest part of the reactor, no large and expensive heating equipment is needed for the reaction. The extremely fast heating makes the reaction practically instantaneous.

Representative reactions between ammonia and hydrocarbons within the scope of the present invention include the following:

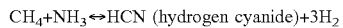
$CH_4 + NH_3 \leftrightarrow HCN \text{ (hydrogen cyanide)} + 3H_2$

$C_2H_6 + NH_3 \leftrightarrow CH_3CN \text{ (acetonitrile)} + 3H_2$

$C_3H_8 + NH_3 \leftrightarrow C_2H_3CN \text{ (acrylonitrile)} + 4H_2$

$C_3H_8 + NH_3 \leftrightarrow C_2H_5CN \text{ (propionitrile)} + 3H_2$

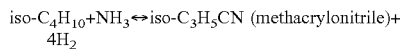
$iso\text{-}C_4H_{10} + NH_3 \leftrightarrow iso\text{-}C_3H_5CN \text{ (methacrylonitrile)} + 4H_2$ Temperatures between 600 and 900° C. are required to overcome equilibrium limitations, because the reactions are highly endothermic.

The high heat needed for the synthesis of these nitriles can be provided as electrical or inductive heating. It is of crucial importance that the heat is provided fast for these reactions to be able to minimize the thermal carbon deposition. Induction heating also provides a more efficient heat transfer to the catalyst particles, unlike that obtained by using a reactor wall medium that is heated externally, which causes loss of heat.

Different heating zones can be effectively employed again with minimum heat transfer losses in a reactor design. As the reactions are highly endothermic, the conversion profile throughout the reactor can be improved by modulating the isothermal conditions at varying parts of the reactor.

It is possible to use bimetallic catalysts, which could also be used as ferromagnetic materials to provide heating for these reactions. Even in case the bimetallic catalysts are not ferromagnetic, they can be mixed with or surrounded by ferromagnetic materials to be used with inductive heating.

The invention is illustrated further in the example which follows below.

Example

The nitrile synthesis is carried out at a low pressure. A mix of alkane or olefinic hydrocarbons with ammonia is used, possibly along with a carrier gas like nitrogen or methane. The gas mixture is heated to 450-550° C. by heat exchange, and then it enters the induction-heated reaction zone.

The induction heater consists, if possible, of a ferromagnetic catalyst with a high electric coercivity (the ability of a ferromagnetic material to withstand an external electric field without becoming depolarized). Alternatively, the catalyst can be mixed with a ferromagnetic material having a high coercivity. This material should be inert towards the gases in the reaction mixture.

The reaction takes place at a reactor temperature between 600 and 800° C., and after leaving the reactor the effluent gas is cooled to a temperature below 200° C. in the feed/effluent heat exchanger. The desired products are separated, while the unconverted hydrocarbons are mixed into the make-up gas.

The invention claimed is:

1. A process for the synthesis of a nitrile by catalyzed reaction of ammonia with a hydrocarbon using heating obtained by passing an alternating current through a metallic coil in a synthesis reactor with a catalyst,
   wherein the endothermic reaction between ammonia and the hydrocarbon takes place in the synthesis reactor with direct inductive heating in a reaction zone,
   wherein the coil is mounted within the synthesis reactor, and all of the catalyst is placed inside the coil.

2. A process for the synthesis of a nitrile by catalyzed reaction of ammonia with a hydrocarbon using heating obtained by passing an alternating current through a metallic coil in a synthesis reactor with a catalyst,
   wherein the endothermic reaction between ammonia and the hydrocarbon takes place in the synthesis reactor with direct inductive heating in a reaction zone,
   wherein the coil is mounted within the synthesis reactor, and the catalyst is placed inside the coil,
   wherein the coil is made of Fe—Cr—Al alloy wire.

3. The process according to claim 1, wherein the inductive heating is carried out using an induction heater which is a ferromagnetic metal structure provided with a suitable coating, and wherein the heating is generated by magnetic hysteresis losses.

4. The process according to claim 3, wherein the metal structure is a metal selected from Fe—Cr and Al—Ni—Co alloys.

5. The process according to claim 4, wherein the metal structure is coated with a porous oxide surface impregnated with a catalytic phase.

6. The process according to claim 5, wherein the catalytic phase contains a catalyst based on Co or Sn.

7. The process according to claim 1, wherein the hydrocarbon is methane, ethane, propane, iso-butane or an olefin.

8. The process according to claim 3, wherein the induction heater comprises a ferromagnetic catalyst.

9. The process according to claim 8, wherein the catalyst is diluted with a magnetic material.

10. The process according to claim 1, wherein the coil is arranged to have a direct electrical contact to the catalyst.

11. The process according to claim 10, wherein the coil is not subject to electrical isolation.

12. The process according to claim 1, wherein the coil is a wire comprising at least one selected from copper, constantan, an iron-chromium-aluminum alloy, and a copper-manganese-nickel alloy.

13. A process for the synthesis of a nitrile by catalyzed reaction of ammonia with a hydrocarbon using heating obtained by passing an alternating current through a metallic coil in a synthesis reactor with a catalyst, wherein the endothermic reaction between ammonia and the hydrocarbon takes place in the synthesis reactor with direct inductive heating in a reaction zone, wherein the coil is a wire comprising at least one selected from copper, constantan, an iron-chromium-aluminum alloy, and a copper-manganese-nickel alloy.

* * * * *